United States Patent [19]

Harper et al.

[11] 4,311,521
[45] Jan. 19, 1982

[54] MEMBRANE SEPARATION OF CATALYST METALS FROM TRIMELLITIC ACID PRODUCTION AND SEPARATION OF COBALT FROM MANGANESE

[75] Inventors: Jon J. Harper, Naperville; Stephen J. Pietsch, Oak Park, both of Ill.

[73] Assignee: Standard Oil Company (Indiana), Chicago, Ill.

[21] Appl. No.: 192,913

[22] Filed: Oct. 1, 1980

[51] Int. Cl.³ .............................................. C22B 3/00
[52] U.S. Cl. ................................. 75/101 BE; 75/109; 75/119; 423/140
[58] Field of Search ................. 562/414; 260/433 R; 423/140; 75/101 BE, 109, 119; 210/321.1, 638, 649, 651

[56] References Cited

U.S. PATENT DOCUMENTS

| | | | |
|---|---|---|---|
| 3,454,490 | 7/1969 | Wallace | 210/321.1 |
| 3,718,583 | 2/1973 | Wu et al. | 210/321.1 |
| 3,940,470 | 2/1976 | Kane et al. | 75/109 |
| 3,957,504 | 5/1976 | Win-Sow Ho et al. | 75/101 BE |
| 4,051,230 | 9/1977 | Miyauchi | 423/658.5 |

*Primary Examiner*—Jacqueline V. Howard
*Attorney, Agent, or Firm*—Fred R. Ahlers; William T. McClain; William H. Magidson

[57] ABSTRACT

Precipitation-free recovery of catalyst metal content of residue from manufacture of trimellitic acid by oxidation with source of molecular oxygen of liquid pseudocumene in presence of cobalt and manganese, cobalt, manganese and cerium, followed by removal of trimellitic acid or its anhydride and, if used, reaction solvent and then separating manganese from the recovered metals. The foregoing is accomplished by extraction of such residue with water, contacting the resulting aqueous extract solution or suspension of insolubles in the aqueous solution with one side of a cation permeable fluoropolymer membrane whose other side is in contact with a hydrohalidic acid to permit metal ions to pass through the membrane, removing the hydrohalidic solution of the catalyst metals, and then after a pH adjustment adding metallic manganese to precipitate cobalt as metal.

6 Claims, No Drawings ered precipitate to the acetate or bromide of the
MEMBRANE SEPARATION OF CATALYST METALS FROM TRIMELLITIC ACID PRODUCTION AND SEPARATION OF COBALT FROM MANGANESE This invention relates to the separation of cobalt and manganese catalyst metals from fluids produced during the manufacture of benzene carboxylic acids and more particularly pertains to such separation of metals by the use of a hydrohalidic acid, a permeable membrane and a fluid residue obtained after substantial benzene carboxylic acid recovery and, if oxidation reaction solvent is used, its substantial removal followed by precipitation of metallic cobalt from the hydrohalidic acid also containing ions of manganese.

STATE OF THE ART

No publication has been found which discloses or even suggests the use of a permeable membrane for the separation of metal oxidation from a fluid residue obtained from the manufacture of a benzene carboxylic acid (i.e., benzoic acid, one of the phthalic acids or one of the benzene tricarboxylic acids).

In general, the separation of metal oxidation catalysts cobalt, manganese or cobalt and manganese from such fluid residue disclosed in publications have been by precipitation of the catalyst metals as carbonates from the residue or aqueous extract thereof, recovery of the metal carbonate precipitate and conversion of the recovered precipitate to the acetate or bromide of the catalyst metal.

U.S. Pat. Nos. 2,964,559; 3,557,173; and 3,673,154 among other patents disclose reclaiming of oxidation metal catalyst cobalt or cobalt and manganese either from the acetic acid mother liquor or a concentrate thereof after separation of such mother liquor and solid iso- or terephthalic acid precipitate from the suspension of such acids in said mother liquor resulting from the liquid phase oxidation of mixed xylenes or m- or p-xylene with air at an elevated temperature above 100° C. in the presence of acetic acid solution of cobalt or cobalt and manganese, generally as their acetates, at an elevated pressure to maintain at least the acetic acid solvent in the liquid phase.

U.S. Pat. No. 2,964,559 teaches that after separating suspended phthalic acids from acetic acid mother liquor and distilling water and acetic acid from said mother liquor leaving a residue, water extraction of the residue reclaims 93% of the cobalt and 94% of the manganese but also extracts 72 mole percent of the phthalic anhydride as the free acid and 80 to 100% of the nickel, iron and chromium present.

U.S. Pat. No. 3,557,173 is concerned with eliminating o-phthalic acid from the cobalt reclaimed from the acetic acid mother liquor. This is done by dehydrating the acetic acid mother liquor (e.g., by addition of acetic anhydride thereto or by distillation of at least 50% of the acetic acid therefrom) whereby anhydrous cobalt acetate precipitates and is recovered by filtration.

U.S. Pat. No. 3,673,154 is concerned with reclamation of cobalt free of iron and chromium. This is done by distilling acetic acid and water from the mother liquor to a pH above 3 (e.g., pH 3.15 to 4.5) which precipitates iron and chromium, removing the Fe and Cr containing precipitate, adding sodium carbonate to precipitate cobalt carbonate and form a soluble form of nickel. Dissolving cobalt carbonate in acetic acid provides the solvent and metal catalyst for the next oxidation of xylene.

Published Japanese patent application No. 14,339/71 is also concerned with the rejection of iron group contaminants and oxygen-containing aromatic compounds from reclaimed Co or Co and Mn catalyst metals. This is accomplished by distilling acetic acid from the mother liquor after phthalic acid product separation. The distillation residue is extracted either with water or aqueous alkaline carbonate (e.g., $Na_2CO_3$) solution. The water extract solution is buffered to a pH of 4.5 to precipitate basic iron acetate. The filtrate after removal of the iron acetate precipitate is treated with sodium carbonate to precipitate cobalt and manganese as carbonates. The extraction with aqueous alkaline carbonate leaves a solid residue which, after recovery from the aqueous solution, is dissolved in an inorganic acid. Buffering the acid solution to pH 4–5 with sodium acetate precipitates iron group metals so that after their removal, Co and Mn can be precipitated as carbonates.

British patent specification No. 1,413,829 is concerned with the rejection of iron group contaminant corrosion metals from cobalt and manganese reclaimed as their carbonates from residues comprising concentrates derived by distilling acetic acid and water from the acetic acid mother liquor after recovery of suspended iso- or terephthalic acid. Such residues are extracted with water in an amount of from 3 to 5 weight parts per weight part of residue because such amounts of water dissolve at 80° C. 90 to 98% of the cobalt and manganese content of the residue and provide an extract solution (after separating insolubles) of pH 3.5–5.0 which dissolves relatively little of the iron group metals present. High quality cobalt and manganese carbonates can be precipitated from such solution after its pH is adjusted preferably to pH in the range of 7 to 8.1 by the use of sodium carbonate and/or bicarbonate.

Said British Patent also discloses that use of water in weight amount equal to the weight of the residue dissolves at 80° C. only 72 to 81% of Co and 66–76% of Mn in the residue.

The foregoing techniques for reclaiming Co and/or Mn, while satisfactory when applied to residues obtained from the production of iso- or terephthalic acid, on their face appear either not applicable to or not suitable for the reclamation of cobalt and manganese from residues obtained from the production of o-phthalic acid or its co-production with trimellitic acid by the respective neat oxidation of liquid o-xylene or liquid mixture of o-xylene and pseudocumene.

It has been discovered in our laboratories that relatively small amounts of water, substantially less than the 16 to 17 to 1 water to residue ratios of U.S. Pat. No. 2,964,559 or the 3:1 to 5:1 water to residue ratios of the British Patent, quite surprisingly will at temperatures of 75° to 80° C., extract more than 90 weight percent of the catalyst metals and less than 25% of the o-phthalic acid from the residues left after the above preparation and recovery of partially purified intramolecular anhydride products and retain the catalyst metals as solutes even at temperatures of 23° C. to 24° C. It has also been found that, although a substantial amount of the oxygen-containing aromatic impurity compounds were also dissolved by the small amount of water, unexpectedly a substantial proportion of the dissolved impurity compounds could be rejected by diluting the extract solution with additional water without substantial change of operating temperature.

From a search of printed publications directed to separation of metal ions from solutions by means of a permeable membrane, the following have been found and are directed to the separation of metal ions which are not commonly used metal catalysts in the production of benzene carboxylic acids.

For example, published Japanese Patent Application (Kokai) Publication No. 53-18244 published 20 February 1978 discloses the separation of ions of metals such as aluminum, copper, lead, zinc, nickel, and chromium from aqueous solutions resulting from anodizing protection or coloration of fabricated aluminum articles. Such solutions have their pH changed twice and, after each pH change, the solution is contacted with a permeable membrane which permits the metal ions to pass through the membrane and deplete the solution's metal ions concentrations. Such schedule of treatment can be an adjustment of pH to a pH greater than 7, contact pH adjusted solution with permeable membrane and collect first metaldepleted solution, adjust its pH to acidic range (pH less than 7), contact acidified solution with permeable membrane, and collect second metal-depleted solution.

In "Ion-Exchange Selectivity and Metal Ion Separations with a Perfluorinated Cation-Exchange Polymer" by H. L. Yeager and A. Steck at pages 862-865 of Analytical Chemistry, Vol. 51, No. 7, June 1979; said article describes the use of powdered sample of Nafion-120 (a polymeric perfluorinated sulfonic acid ion exchanger of Du Pont and Co.) for hydrogen ion exchange with alkali metal and silver ions in aqueous solution, sorbed water and cation diffusion. No useful purpose for such metal ion separations was mentioned in said article.

U.S. Pat. No. 4,186,084 issued Jan. 29, 1980 is directed to diaphrams for chloralkali electrolytic cells prepared from fluoropolymers chemically modified with sulfur (e.g., in sulfonyl, suffinyl and sulfuryl halide, mercaptons, metal mercaptides, thio acids, metal salts of thio acids esters of mono- and dithio acids) or phosphorus (e.g., in tetrathiophosphoric acid and metal salts thereof; phosphonic acid, metal salts and esters thereof; phosphorous acid and salts thereof; and halides of phosphorous and phosphonic acid). Such diaphrams do effectively separate alkali metal ions from aqueous solution also containing chlorine ions.

U.S. Pat. No. 3,450,630 is directed to separations of one metal ion from other metal ions by the use in electrolytic cell of electrically uncharged membranes of polymeric matrices having etheric oxygen and/or carbonyl groups. Said polymeric matrices are derived from polyvinyl chloride, copolymers of ethylene and vinyl acetate, copolymer of methyl-methacrylate and vinyl acetate, polyvinyl methylketone, copolymer of vinyl methylketone and vinyl acetate, polyalkyl acrylates, copolymer of methyl isopropylketone and methylmethacrylate, copolymer of methylmethacrylate and butylacrylate, and copolymer of vinyl acetate and acrylonitrile.

U.S. Pat. No. 3,450,631 is directed to separations of metal ions of a preselected species from metal ions of another species having the same charge and similar ionic diameter involving permeating the preselected species through an ion-specific membrane comprising supported polyvinyl chloride polymer film plasticized by an organo-phosphorus compound. Specifically uranium ions were removed from admixture with iron and aluminum ions in aqueous solution by uranium permeation through supported plasticized PVC membrane into water on the other side of the membrane.

U.S. Pat. No. 3,408,315 is directed to the production of a microporous polyamide membrane useful for separation of microorganisms, cells and minute particles from various liquids, gases or for sterilizing biological solutions by filtration of the solution.

U.S. Pat. No. 3,149,179 is directed to the separation of alkyl, oxyalkyl and thioalkyl aluminums from linear olefins by contacting the mixture with a chemically resistant, semi-permeable plastic (e.g., polyolefin such as polyethylene)membrane.

As the above state of the art indicates it is of little or no use for devising a method of separating catalyst metals from residual fluids from benzene carboxylic acid manufacture. Such residual fluids contain methyl-hydroxymethyl-, formyl-substituted benzene toluene and xylene or benzoic acid, benzaldehyde, or phthalic acid together with the benzene carboxylic acid.

There is a further need to separate cobalt from manganese so that each can be separately used for staged addition; for example, cobalt only is used until from 2 to 2.5 moles of oxygen per mole of pseudocumene is consumed and thereafter manganese is added as the oxidation continues. Such staged addition of catalyst metals is disclosed and claimed by U.S. Pat. No. 3,491,144. Also, according to U.S. Pat. No. 3,683,016 the oxidation of pseudocumene to trimellitic acid requires two or more oxidation steps, each of which have different concentrations of manganese based on pseudocumene charged with the concentration of manganese increasing from the first to the last step.

Thus, for the oxidation of pseudocumene to trimellitic acid there is a need to separately recover each of cobalt and manganese from the oxidation process residue.

The state of the art has no disclosure or suggestion for said special need to separate cobalt from manganese. However, such a separation has now been discovered and such discovery comprises the subject inventive contribution whose description immediately follows.

SUMMARY OF THE INVENTION

It has now been discovered that the catalyst metals can be separated from the fluid residue of the manufacture of trimellitic acid by extracting the fluid residue with water at a temperature of from 25° C. up to 100° C. with from 0.25 up to 6 weight parts, preferably 0.35 to 3, and more preferably 0.6 to 1.0, weight parts, water per weight part of residue, contacting the extract solution or the suspension of insolubles in said solution with one side of a cation permeable fluoropolymer membrane whose other side is contacted with a hydrohalide acid such as hydrochloric or hydrobromic acid followed by adjusting the pH of the hydrohalidic acid after such contact to precipitate metallic cobalt at a pH of 6 and then magnetically separating the cobalt precipitate from the solution of manganous ions.

The preferred cation permeable membrane can be a flat film or tubing of a polytetrafluoroethylene modified by sulfonic acid groups attached to chain carbon atoms.

Ions of the catalyst metals pass through the membrane but most of the water-soluble aromatic compounds including the carboxylic acid-substituted aromatic compounds do not pass through the membrane. Some of the water solvent for the catalyst metals also pass through the membrane.

Such separation of catalyst metals does not occur when acetic acid, phosphoric acid, sulfuric acid or nitric acid is on the side of the membrane opposite the aqueous extract solution of the aromatic process residue.

The compositions of residues from the manufacture of trimellitic anhydride by the catalytic air oxidation of pseudocumene (1,2,4-trimethylbenzene) are shown in TABLE I.

TABLE I
CHARACTERIZATION OF RESIDUES FROM THE MANUFACTURE OF TRIMELLITIC ACID (TMLA) AND TRIMELLITIC ANYHDRIDE (TMA)

| Component, In Weight % | RESIDUE TMLA | TMA |
|---|---|---|
| Acetic Acids | 1.58 | 0 |
| Phthalic Acids | 12.3 | 1.0 |
| Aldehydes | 0.53 | 1.4 |
| Benzoic Acid | 0.5 | 0 |
| Trimellitic Aid | 38.6 | 65.2[1] |
| OLB Compounds[2] | 4.7 | 1.9 |
| HB Compounds[3] | 0.94 | 0.4 |
| Cobalt | 1.17 | 2.51 |
| Manganese | 0.28 | 0.87 |
| Bromine | 0.94 | 0.15 |

[1] Trimellitic acid anhydride
[2] "OLB Compounds" are other lower boiling componds.
[3] "HB Compounds" are higher boiling (higher than trimellitic acid) compounds.

When oxidation and/or product recovery process apparatus contains elements fabricated from corrosion resistant steel or corrosion resistant alloys containing iron as an impurity or rather minor alloy modifier, the residue to be extracted can contain an iron salt. Then iron ions appear in the extract solution. In this case the iron is removed from the extract solution by first adjusting its pH to from 4 to 5 causing iron hydroxide to precipitate. After removing iron hydroxide precipitate the resulting modified extract solution is treated to precipitate cobalt by pH adjustment to pH 6 and treatment with powdered metallic manganese in a gram atom amount chemically equivalent to the dissolved cobalt. The manganese goes into solution replacing the precipitated cobalt. While ribbons, pellets, etc. of manganese might be used in place of the powdered form, the larger forms of manganese become ineffective due to the metallic cobalt plating a coating on them. Such efficiency reducing plating does not appear to occur when powdered manganese is used.

For the pH adjustments any alkaline material can be used, for example, alkali and alkaline earth metals, their oxides, hydroxides and carbonates as well as ammonium hydroxide. Preferably ammonium hydroxide is used to effect the pH changes because the alkali and alkaline earth metals used as their oxides, hydroxides adds to dissolved solids waste load in the waste disposal system of the manufacturing plant.

EXAMPLE 1

Conduct of the present invention is illustrated by the following examples wherein the aqueous extract (24° C.) of trimellitic acid process residue (water to residue ratio of 2:1.0) is placed in a glass cylinder closed at its bottom with a permeable membrane film of polytetrafluoroethylene modified by sulfonic acid groups bonded to carbons of the polymer chain. Said cylinder is placed with the membrane at the bottom in a chamber which contained hydrochloric acid (37 wt.% HCl). Both the extract solution and the hydrochloric acid are stirred. The catalyst metals content in grams initially in the aqueous solution, finally in the hydrochloric acid and remaining in the depleted aqueous solution are reported in TABLE V below:

TABLE V
EXTRACTION OF METALS FROM AQUEOUS SOLUTION BY CATION PERMEABLE FLUOROPOLYMER MEMBRANE

|  | Cobalt | Manganese | Cerium |
|---|---|---|---|
| Initial H$_2$O Solution | 0.115 | 0.065 | 0.06 |
| Final HCL Solution | 0.089 | 0.048 | 0.052 |
| Depleted H$_2$O Solution | 0.026 | 0.017 | 0.008 |

The foregoing demonstrates that about 77% of the cobalt, 74% of the manganese and 87% of the cerium passed through the membrane and into the hydrochloric acid.

EXAMPLE 2

The catalyst metals cobalt, manganese and cerium are separated from residue, fluid when made, from the manufacture of trimellitic acid in a continuous flow system in the following manner.

The hot (200° C.) fluid residue at 2.4 kg per hour is mixed with 2.4 kg per hour of water at a temperature of 25° C. The resulting slurry of insolubles suspended in extract solution cooled to 100° C. by indirect heat exchange is pumped through coils tubing of cation permeable polytetrafluoroethylene modified by sulfonic acid groups attached to chain carbon atoms. Said coils are in a vessel containing hydrochloric acid (37 wt% HCl) flowing through the vessel at 4 kg per hour. The outflow of hydrochloric acid containing the catalyst metals passing through the cation permeable polymeric tubing amounts to 5.0 kg per hour. Such outflow hydrochloric acid is contacted in indirect heat exchange with the slurry of insoluble suspended in extract solution whereby 4.0 kg per hour of hydrochloric acid (HCl and water vapor) are driven off, condensed and recycled to the catalyst metal permeation exchange. The remaining 1.0 kg of solution contains the catalyst metals as chloride solutes.

The 1.0 kg per hr solution of catalyst metal chlorides includes iron chloride. The iron ions resulting from corrosion of apparatus elements fabricated from stainless steel. To the 1.0 kg solution of catalyst and corrosion metals there are added 270 grams per hour of aqueous ammonium hydroxide (28 to 30 wt.% NH$_3$) to increase the solution's pH to precipitate iron as ferrous hydroxide. The suspension of ferrous hydroxide in the pH adjusted solution of metal chlorides is charged to a solid-liquid separator (centrifuge, filter, etc.) to separate the solution and reject the ferrous hydroxide, about 10.9 grams per hour. The separated solution, 1.250 kg per hour, one gram per hour of ammonium hydroxide is added to bring the solution to pH of 6 and 14 grams per hour of powdered manganese are combined to precipitate cobalt as metal particles. The suspension of cobalt metal particles in the solution of manganese chloride is passed over a magnetic separator where, in this case 10.9 grams, cobalt metal particles are collected and 1.22 kg per hour of aqueous solution of manganous and ammonium chlorides are separated.

The 10.9 grams per hour of cobalt metal particles are washed free of aqueous solution of manganous and ammonium chlorides and then mixed with 62 grams per hour of hydrobromic acid (47 wt.% HBr) whereby 72.9 grams of cobalt bromide solution (14.95 wt.% Co) is formed.

The solution, 1.22 kg per hr, of manganous and ammonium chlorides is used as the manganese source for pseudocumene oxidation as before described.

The effluent from the cation permeable tubes amounts to 4.6 kg per hour, is essentially metal free and is useful as feed to an evaporation system conducted in one or two series connected wiped film evaporators for removal of solvent water and water of dehydration of trimellitic acid to its intramolecular anhydride and evaporation of said anhydride and lower boiling organic impurities from higher boiling impurities. Then by either partial condensation or a combination of total condensation and distillation trimellitic acid anhydride (4-carboxyphthalic anhydride) in an amount of about 0.6 kg per hr. can be recovered.

The invention claimed is:

1. A method of separately recovering cobalt and manganese from residue obtained by removal of substantial trimellitic acid and, if used, reaction solvent from the product of the oxidation with a source of molecular oxygen of liquid pseudocumene in the presence of cobalt and manganese as metal oxidation catalyst, which method comprises extracting the residue with from 0.25 up to 6 weight parts of water per one weight part of residue at a temperature of from 25° C. up to 100° C., contacting at a temperature of from 25° C. up to 100° C. the extract solution or combination of said solution and insoluble portion of the residue with one side of a cation permeable fluoropolymer membrane whose other side is in contact with hydrochloric acid or hydrobromic acid, upwardly adjusting the pH of the hydrochloric or hydrobromic acid solution now containing ions of the catalyst metals to a pH of 6 while adding powdered manganese in a gram atom amount chemically equivalent to the dissolved cobalt to precipitate it as metallic cobalt, and recovering such metallic cobalt with magnetic separator thereby providing an aqueous solution of manganese.

2. The separatory method of claim 1 wherein the cation permeable membrane is a polyfluoroethylene modified by sulfonic acid groups attached to chain carbon atoms.

3. The separatory method of claim 2 wherein the residue also contains iron, the pH of the extract solution is first adjusted to pH 4 to 5 to precipitate ferrous hydroxide, and after separation of the ferrous hydroxide precipitate the remaining aqueous solution's pH is then adjusted to pH 6.

4. The separatory method of claim 3 wherein each pH adjustment is made with an alkali metal or ammonium hydroxide.

5. The separatory method of claim 4 wherein the weight ratio of water to residue is 0.35:1 up to 3:1 and the pH adjustment is made with ammonium hydroxide.

6. The separatory method of claim 5 wherein the weight ratio of water to residue is 0.6:1 up to 1:1.

* * * * *